(12) United States Patent
Ryczek

(10) Patent No.: US 7,039,460 B2
(45) Date of Patent: May 2, 2006

(54) DEFIBRILLATOR WITH RETRACTABLE CABLE

(75) Inventor: Kevin R. Ryczek, Methuen, MA (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 560 days.

(21) Appl. No.: 10/170,936

(22) Filed: Jun. 13, 2002

(65) Prior Publication Data

US 2003/0233127 A1    Dec. 18, 2003

(51) Int. Cl.
*A61N 1/39* (2006.01)

(52) U.S. Cl. ............................................ 607/5; 607/37

(58) Field of Classification Search ............ 607/36–38, 607/1–2, 4–5, 10, 508–509; 439/909; 242/371–385.4
See application file for complete search history.

(56) References Cited

U.S. PATENT DOCUMENTS

| | | | | |
|---|---|---|---|---|
| 1,247,358 A | * | 11/1917 | Zwilling | ................ 191/12.2 R |
| 3,964,490 A | * | 6/1976 | Nelms | ........................... 607/2 |
| 4,713,497 A | * | 12/1987 | Smith | .................... 191/12.2 R |
| 6,205,355 B1 | * | 3/2001 | Lomanto et al. | ............ 600/509 |
| 6,327,507 B1 | * | 12/2001 | Buchan | ....................... 607/115 |

* cited by examiner

*Primary Examiner*—Robert E. Pezzuto
*Assistant Examiner*—Kristen Mullen
(74) *Attorney, Agent, or Firm*—Tony Piotrowski

(57) ABSTRACT

An apparatus for using automatically retractable cables with a defibrillator. The Apparatus provides (a) a defibrillator comprising a power source electrically connected between a first wire and a second wire; and (b) an automatic rotatable housing automatically retracting the first wire and the second wire wound around the rotatable housing. A circular spring can also be used to exert rotational force on the rotatable housing and connect the cables to the power source.

4 Claims, 4 Drawing Sheets

DEFIBRILLATOR WITH RETRACTABLE CABLE

BACKGROUND OF THE INVENTION

1. Field of the Invention

The present invention is directed to using a circular housing with a retractable cable for use with a defibrillator. Using such a housing provides a more convenient way for operators of defibrillators to utilize the cables as well as store the cables when operation is complete.

2. Description of the Related Art

Current defibrillators utilize cables in order to apply electric energy to a shock a patient's heart and monitors a patient's vital signs. Typically these cables are stored in a pouch, which means that the operator must manually collect the cable when operation is complete and place the cable in some type of collection device on the defibrillator, such as an internal pouch. This procedure is conducive to tangling of the cables, which can also cause damage to the cables.

Therefore, what is needed is an easy, neat, and non-damaging way for an operator of a defibrillator to extract the defibrillator cables from a defibrillator and replace them when operation of the defibrillator is completed.

SUMMARY OF THE INVENTION

It is an aspect of the present invention to provide an improved defibrillator, which allows for easy application and retraction of the defibrillator cables.

It is another aspect of the present invention to use circular spring(s) to power defibrillator cables, providing a more reliable apparatus.

The above aspects can be attained by a system that provides a defibrillator comprising a defibrillator comprising a power source providing an electrical current between a first wire and a second wire; and first circular rotatable housing connected to the defibrillator and automatically receiving the first wire wound around the first circular rotatable housing.

These together with other aspects and advantages which will be subsequently apparent, reside in the details of construction and operation as more fully hereinafter described and claimed, reference being had to the accompanying drawings forming a part hereof, wherein like numerals refer to like parts throughout.

DETAILED DESCRIPTION OF THE PREFERRED EMBODIMENTS

Figure 1:
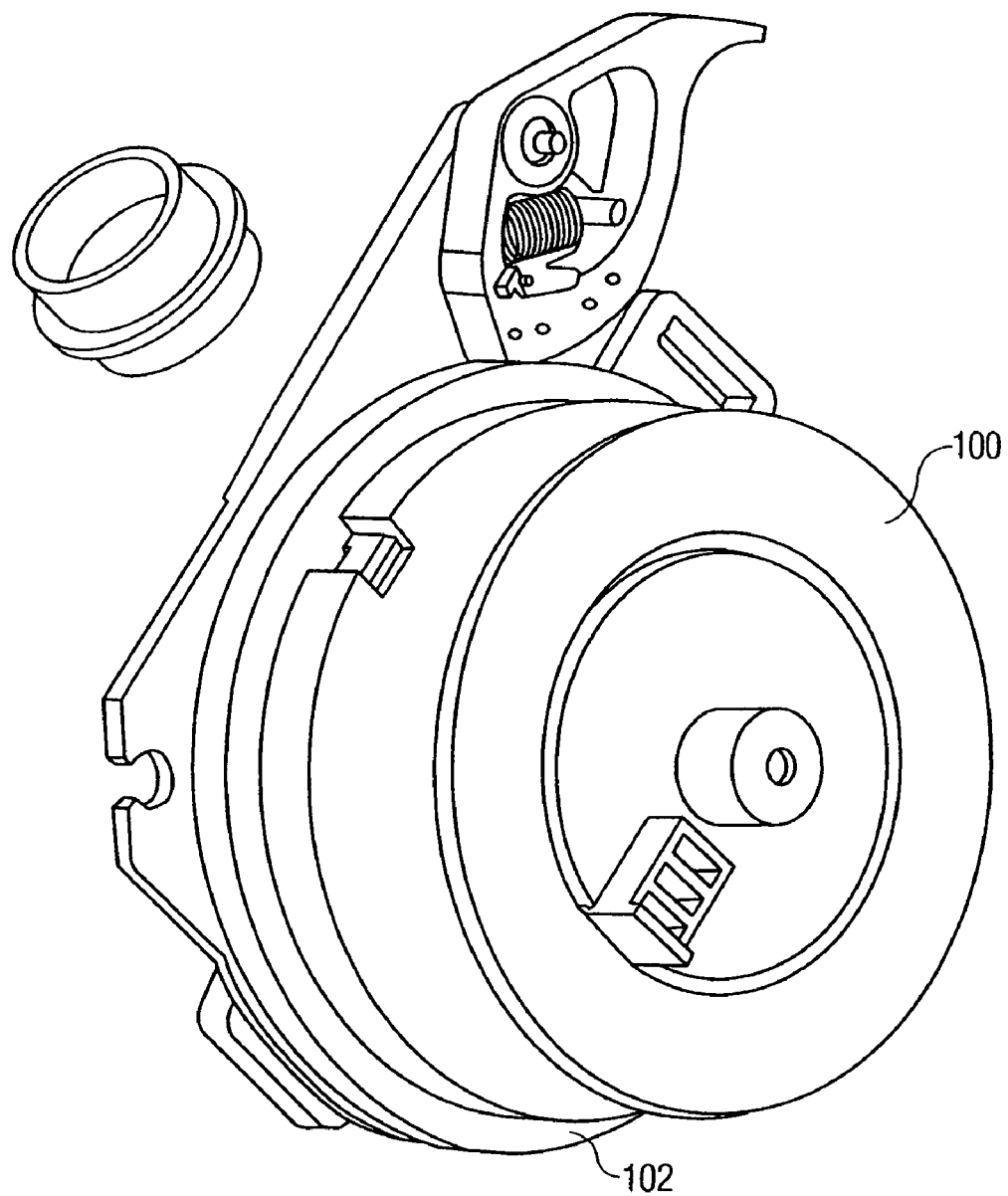
FIG. 1 illustrates a circular housing for a retractable cable, according to an embodiment of the present invention.

Reference will now be made in detail to the present preferred embodiments of the present invention, examples of which are illustrated in the accompanying drawings, wherein like reference numerals refer to the like elements throughout.

The present invention provides for a defibrillator which implements an automatically retractable cable in a circular housing, allowing an operator to automatically retract the cable when operation of the defibrillator is complete by pressing a button on a braking device.

Other retractable cable devices (not used with defibrillators, but for example vacuum cleaners), have numerous disadvantages. One such device may operate by manually winding an electrical cable with an electrical outlet plug at one end around a hook type device. The cable consists of two twisted wires, and the ends of each wire (at the opposite end than the plug) are connected to a disc in the middle of the housing. The outside of the disc contains two electrical conductive grooves or tracks, one connected to each wire. Two "runners" on the outside of the disc contact each groove (or track) and connect to terminals inside the device receiving the power from the electrical outlet. In this way, the cable can be pulled, the disc can rotate, and the runners on the outside of the disc remain in contact with the wires, which receive power from the plug.

However, the type of devices described above have numerous disadvantages. These devices contain moving parts, which can wear on the contacts. Also the runners may over use become misaligned from the grooves, providing no power to the device at all. Also, either the track or runner may wear over time. If the wearing is sufficient, then power again may not be provided across this track/runner junction to the paddles. When using a life-saving device such as a defibrillator, there is no room for a malfunctioning device.

In order to improve deficiencies in the above described devices, the present invention uses a spring-loaded apparatus utilizing a circular spring in order to provide an improved and more reliable device.

FIG. 1 illustrates a circular housing for a retractable cable, in one embodiment of the present invention.

A circular housing 100 is used to receive a cable (not illustrated). A receiving unit 102 receives the cable wound around the receiving unit 102.

Figure 2:
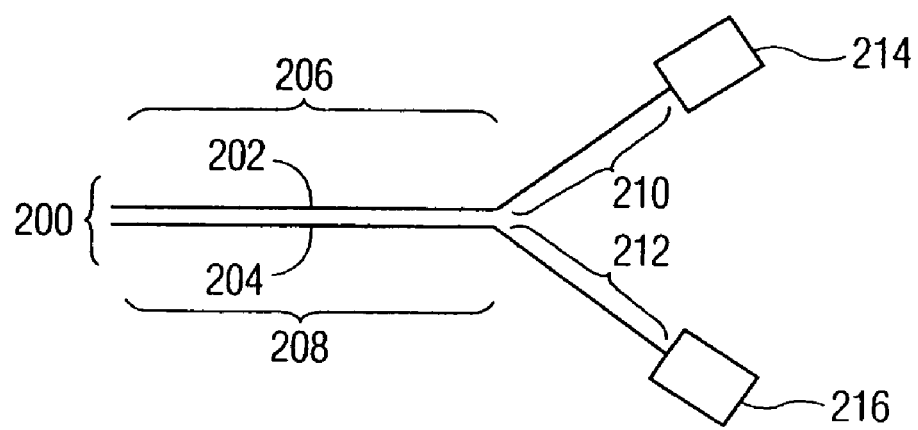
FIG. 2 illustrates a cable, according to an embodiment of the present invention.

FIG. 2 illustrates a cable used for a defibrillator, according to one embodiment of the present invention.

The cable 200 comprises a first wire 202 and a second wire 204. A first portion 206 of the first wire 202 and a first portion 208 of the second wire 202 are fused or clamped together, even though both wires are insulated. A second portion 210 of the first wire 202 and a second portion 212 of the second wire 204 are separate. The first wire 202 and second wire 204 carry opposite charges to be applied to a patients chest. These portions are separate so that a first paddle 214 and a second paddle 216 can be applied at different parts of the patient's chest. The length of the first portion of the first wire, the first portion of the second wire, the second portion of the first wire, and the second portion of the second wire can all be set arbitrarily, although typically the length of the first portions of both wires are equal, and typically the length of the second portions of both wires are equal.

Figure 3:
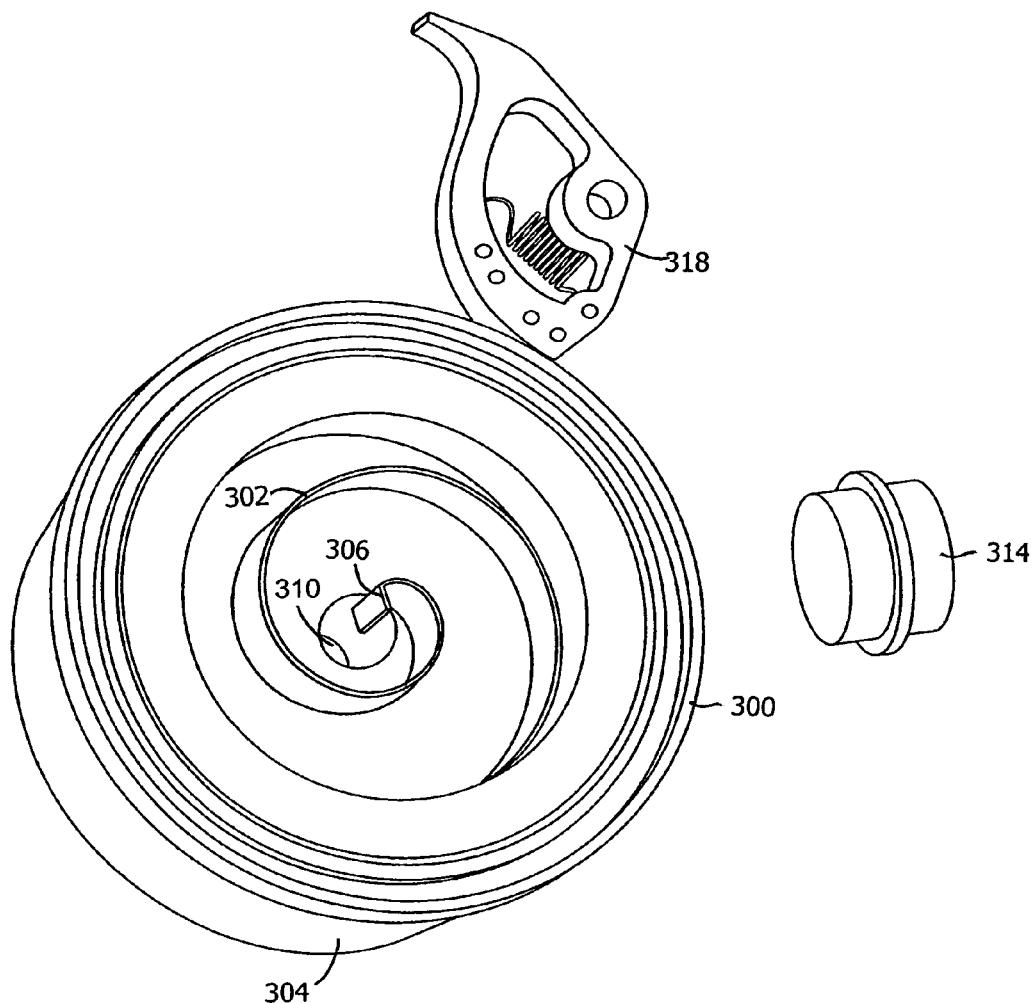
FIG. 3 illustrates an inside view of a circular housing for a retractable cable, according to an embodiment of the present invention.

FIG. 3 illustrates a circular housing for a retractable cable, according to one embodiment of the present invention.

A circular housing 300 comprises a first circular spring 302. As stated above, a cable (not pictured) comprises a first wire (not pictured) and a second wire (not pictured). The cable wraps around the circular housing 300 and into a receiving unit 304. A first end 306 of the circular spring 302 is located in the middle 310 of the circular housing 300. A second end (not pictured) of the circular spring 302 is connected through a hole (not pictured) in the circular housing 300 to an end of the first wire (not pictured).

When the cable is pulled, the circular housing 300 rotates in a first direction, which causes the first circular spring 302 to store energy. When the cable is released, the stored energy in the first circular spring 302 causes the circular housing 300 to rotate in an opposite direction, pulling the cable towards the circular housing 300 and winding the cable around the circular housing 300. A first cap 314 attaches into a middle 310 of the circular housing 300, keeping the first end 306 of the circular spring 302 in the middle 310 of the circular housing 300. The first cap 314 can be attached in any conventional way, for example snapping onto a receiving part, or by using an adhesive.

A first electrical connector (not pictured) connects the first end 306 of the circular spring 302 to a first terminal on a power source (not pictured). In this way, the power source is connected to the first wire through the first circular spring 302. If this circular spring is considered as a typical tape measure with the tape wound-up inside its housing, then there are two ends to the tape measure: one that is at the outer edge of the housing and one that remains in the center of the housing. When the tape measure is in its rolled up position, there is also a distinct top and bottom face to the tape. Unlike the tape measure, the circular spring of the present invention is not pulled out of its housing. Instead, the end of the circular spring that is at the center is allowed to expand and contract slightly when our cable is extracted and retracted. This occurs because this end of the circular spring is attached to the center of the plastic housing that holds the paddle cables and thus rotates when the cables are extracted. This rotation results in the expansion and contraction of the circular spring.

Power to one paddle through the plastic housing is provided by connecting a copper wire from the end of the spring that remains at the center of the device to the paddle cable which is wrapped up in the housing. This copper wire could be either fused or clamped along the bottom portion of this spring end. Since this end of the spring is also attached to the center of the plastic housing, the copper wire connecting the paddle cable and this end of the spring does not twist when the cable is extracted. This is on account that all of the above pieces (cable, housing, wire and this end of the spring) rotate as one when the cable is extracted.

Power to the defibrillator through the plastic housing would use the opposite end of the spring, which is further away from the center of the device. A separate copper wire would be clamped or fused to this end of the spring and would protrude out from the top face of the spring. Since this portion of the spring is attached to stationary plastic cap and thus does not rotate, this copper wire can directly extend out of the top face of the cap and to the defibrillator.

The second paddle, cables, and spring mechanism would be setup similarly, but only on the other side of the plastic housing. The two paddle cables would wind up along the center of the mechanism and in between the two circular springs. Both springs are, thus, used to retract these two paddle cables. For ease of storage, these two paddle cables could be molded into one cable, but the wires would still have to be insulated from each other.

While not pictured, on an opposite side of the circular housing 300, a second circular spring is present which operates in the same manner as the first circular spring 302 the second circular spring connects the second wire to a second terminal on the power source.

Since the first wire and the second wire are attached at first portions of these wires, having two springs increases the force applied to the cable (or first wire and second wire) when they are retracted.

Both springs are insulated from each other, and a divider can be used to separate the springs from each other. The divider can be the circular housing 300 which holds the wrapped cables.

Any conventional braking device 318 can be used to allow the cable (first wire and second wire) to be pulled outward from the circular housing 300, but not automatically retracted in the reverse direction. A button on the braking device (not pictured) is pressed, which releases a locking mechanism and allows the circular springs to automatically retract the cable.

One implementation of a braking device can be implemented by using a tear-shaped plastic or rubber stopper, which is in constant contact with the plastic housing which rotates when the cables are extracted or retracted. This stopper is spring-loaded into position from the plastic housing and allows the housing to easily rotate in the extraction direction. Because of its tear like shape, rotation in the retraction direction is much more difficult until a button is pushed to release the spring. The stopper is then released from the housing and the circular springs are allowed to retract the cables.

The stopper is typically pressed by a spring, which restricts the housing from rotating in the retraction direction. When the spring is released by pressing of the button (or any other release mechanism), the stopper is released, allowing the circular springs to retract the cables.

Figure 4:
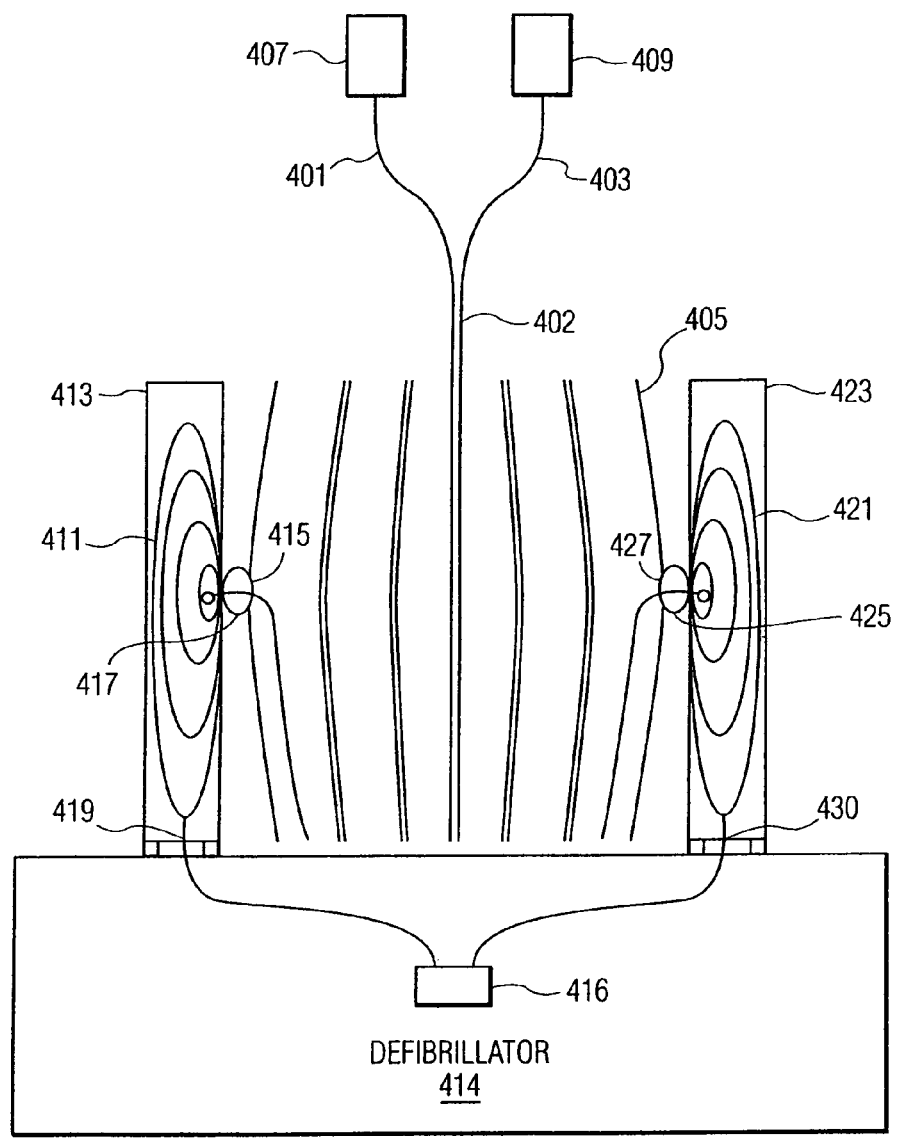
FIG. 4 illustrates a defibrillator with retractable cable, according to an embodiment of the present invention

FIG. 4 illustrates a defibrillator with a retractable cable, according to an embodiment of the present invention. Left cable 401 and right cable 403 are wrapped around the rotatable housing 405. Left cable 401 and right cable 403 are used to apply a charge to paddles 407 and 409, respectively Note left cable 401 and right cable 403 are insulatedly fused together except at two parts. The first part where the left cable 401 and right cable 403 are separated is at a breaking point 402 of the left cable 401 and right cable 403 so that the left paddle 407 and right paddle 409 can be separated. The second part where the left cable 401 and the right cable 403 are separated is an opposite end of the breaking point 402 so the left cable 401 can be connected to a different location than the right cable 403 (to be discussed below).

A left circular spring 411 is housed in a left housing 413. The left circular spring serves two purposes. One purpose is to apply a rotational force to the rotatable housing 405 so that the rotatable housing 405 automatically retracts (when a braking mechanism, not illustrated in FIG. 4, is not applied). Another purpose of the left circular spring 411 is to electrically connect left cable 401 with a power source 416 in the defibrillator 414.

The left cable 401 runs through an opening 415 in the rotatable housing 405, through a left cap 417, and electrically connects to the left circular spring 411. The left cap 417 typically connects the rotatable housing 405 to the left spring housing 413 and rotates with a center of the left circular spring 411. The left circular spring 411 contains a bottom opening 419 so that the left cable 401 can connect to the power source 416.

A right circular spring 421 is housed in a right housing 423. The right circular spring 421 serves the same purpose as the left circular spring 411. The right cable 403 runs through an opening 425 in the rotatable housing 405, through a right cap 427, and electrically connects to the right circular spring 421. The right cap 427 typically connects the rotatable housing 405 to the right spring housing 423 and rotates with a center of the right circular spring 421. The right circular spring 421 contains a bottom opening 430 so that the right cable 403 can connect to the power source 416.

The rotatable housing 405 rotates with the left cap 417 and the right cap 427 when then left cable 401 and/or the right cable 403 is pulled, winding both the left circular spring 411 and the right circular spring 421. Note that due to the nature of circular springs, their centers will rotate while their outsides will typically stay stationary. Outsides (i.e. an end point or a perimeter) of the left circular spring 411 and the right circular spring 421 may also be physically attached to a bottom of each respective housing, fixing the outsides of the springs 411,421 into place. Thus a center of both circular springs 411, 421 is able to rotate with the caps 417,427 and the rotatable housing 406, while an end portion (or perimeter) of the circular springs 411,421 is able to remain stationary. Note the left housing 413 and the right housing 423 remains stationary. Left housing 413 and right housing 423 is mounted onto the defibrillator 414. For example, the left housing 413 and the right housing 423 can be snapped or screwed onto the defibrillator 414. Note that of course left cable 401 and right cable 403, and all of their respective electrical connections, remain insulated from each as to not short circuit the electrical potential between paddles 407, 409.

This configuration allows the power source 416 of the defibrillator 414 to power the paddles 407, 409 using circular springs 411, 421. This provides more a more reliable system, since no runners or grooves are required which can become worn and bent. The problem of misalignment of the conducting apparatus is solved. Using a rotatable housing with a defibrillator is also is beneficial over the prior art in that no manual collection of the cables is required.

Other variations of the invention including using only one circular spring instead of two, and connecting the remaining defibrillation cable by conventional methods.

The many features and advantages of the invention are apparent from the detailed specification and, thus, it is intended by the appended claims to cover all such features and advantages of the invention that fall within the true spirit and scope of the invention. Further, since numerous modifications and changes will readily occur to those skilled in the art, it is not desired to limit the invention to the exact construction and operation illustrated and described, and accordingly all suitable modifications and equivalents may be resorted to, falling within the scope of the invention.

What is claimed is:

1. A defibrillator apparatus comprising:
   a power source electrically connected between a first wire and a second wire; and
   an automatic rotatable housing having a center plane and automatically retracting the first wire and the second wire wound around the rotatable housing,
   further comprising a first circular spring located on a first side of the center plane and electrically connecting the first wire with a power source of the defibrillator on the first side of the center plane,
   further comprising a nonconductive first spring housing which houses the first circular spring, a middle of the first circular spring electrically connected to the first wire, and a perimeter of the first circular spring electrically connected to a first terminal of the power source,
   further comprising a second circular spring located on a second side of the center plane and electrically connecting the second wire with a power source of the defibrillator on the second side of the center plane,
   further comprising a nonconductive second spring housing which houses the second circular spring, a middle of the second circular spring electrically connected to the second wire, and a perimeter of the second circular spring electrically connected to a second terminal of the power source,
   wherein the rotatable housing rotates while the first and second spring housings remains stationary.

2. An apparatus as recited in claim 1, wherein the middle of the first and second circular springs rotate with the circular housing, while the perimeters of the first and second circular springs remain stationary.

3. An apparatus as recited in claim 2, wherein a rotatable first cap is attached to the middle of the first circular spring through a center of the circular housing, and a rotatable second cap is attached to the middle of the second circular spring through a center of the circular housing.

4. A defibrillator apparatus, comprising:
   a power source electrically connected between a first wire and a second wire;
   an automatic rotatable housing automatically retracting the first wire and the second wire wound around the rotatable housing;
   a first circular spring electrically connecting the first wire with a power source of the defibrillator;
   a second circular spring electrically connecting the second wire with a power source of the defibrillator;
   a nonconductive first spring housing which houses the first circular spring, a middle of the first circular spring electrically connected to the first wire, and a perimeter of the first circular spring electrically connected to a first terminal of the power source;
   a first locking device preventing the circular housing from rotating; and
   a button on the first locking device which releases the circular housing and automatically allows the rotatable housing to retract the first wire using energy from the first circular spring,
   wherein the first circular spring exerts a rotational force retracting the first wire into the rotatable housing,
   wherein the rotatable housing rotates while the nonconductive first spring housing remains stationary,
   wherein the middle of the first circular spring rotates with the circular housing, while the perimeter of the first circular spring remains stationary,
   wherein a rotatable first cap is attached to the middle of the first circular spring through a center of the circular housing,
   wherein the first circular spring and the second circular spring are insulated from each other,
   wherein a first portion of the first wire and a first portion of the second wire are insulatedly attached, and a second portion of the first wire and a second portion of the second wire are separate.

* * * * *